United States Patent
Haecker et al.

(10) Patent No.: US 9,579,438 B2
(45) Date of Patent: Feb. 28, 2017

(54) RETAINING MEANS FOR RETAINING AN EXTERNAL FUNCTIONAL MEANS ON A TREATMENT APPARATUS, EXTERNAL FUNCTIONAL MEANS, AND TREATMENT APPARATUS

(75) Inventors: Jurgen Haecker, Neu-Anspach (DE); Uwe Lapp, Butzbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 644 days.

(21) Appl. No.: 12/765,940

(22) Filed: Apr. 23, 2010

(65) Prior Publication Data
US 2010/0270225 A1 Oct. 28, 2010

Related U.S. Application Data

(60) Provisional application No. 61/185,614, filed on Jun. 10, 2009.

(30) Foreign Application Priority Data

Apr. 23, 2009 (DE) .................. 10 2009 018 664
Jun. 10, 2009 (DE) .................. 10 2009 024 448

(51) Int. Cl.
*B01D 35/30* (2006.01)
*A61M 1/16* (2006.01)
(Continued)

(52) U.S. Cl.
CPC ............... *A61M 1/16* (2013.01); *A61M 1/34* (2013.01); *A61M 5/1417* (2013.01);
(Continued)

(58) Field of Classification Search
CPC ........ A61M 2209/08; A61M 2209/084; A61M 2209/086; A61M 2209/088; A61M 5/1414; A61M 5/1415; A61M 5/1417; A61M 2209/082; A61M 5/1418; A61M 1/1652; F16M 11/041; B01D 35/306;
(Continued)

(56) References Cited

U.S. PATENT DOCUMENTS 3,603,550 A * 9/1971 Byrd ............................ 248/313
4,211,380 A * 7/1980 Lillegard et al. ........ 248/229.15
(Continued)

FOREIGN PATENT DOCUMENTS

DE       24122 58 A1    9/1975
DE       3912405 C1    10/1990
(Continued)

OTHER PUBLICATIONS

International Search Report for PCT/EP2010/002493 mailed on Oct. 13, 2010.

*Primary Examiner* — David C Mellon
*Assistant Examiner* — Pranav Patel
(74) *Attorney, Agent, or Firm* — Fish & Richardson P.C.

(57) ABSTRACT

The present invention relates to a retaining device for retaining at least one external functional apparatus comprising at least two tube ports on a treatment apparatus, wherein the retaining device comprises at least two stops which restrict a rotational movement of the external functional apparatus inside the retaining device. It further relates to an external functional apparatus as well as a treatment apparatus.

17 Claims, 9 Drawing Sheets

(51) Int. Cl.
*A61M 1/34* (2006.01)
*A61M 5/14* (2006.01)

(52) U.S. Cl.
CPC ............ *A61M 2209/082* (2013.01); *B01D 2201/4023* (2013.01); *B01D 2201/4076* (2013.01); *B01D 2201/4084* (2013.01)

(58) Field of Classification Search
CPC ...... B01D 2201/4023; B01D 2201/307; B01D 2201/4046–2201/4061; B01D 2201/4076; B01D 2201/4084; B01D 61/20; B01D 46/2414
USPC .... 210/321.6, 234, 450, 232, 418, 455, 239, 210/240, 235, 237, 443; 248/313, 154, 248/311.2, 316.1
See application file for complete search history.

(56) References Cited

U.S. PATENT DOCUMENTS

| | | | |
|---|---|---|---|
| 4,586,687 A * | 5/1986 | Ziaylek, Jr. ................ | 248/313 |
| 4,989,909 A * | 2/1991 | Bouligny et al. .......... | 294/119.3 |
| 5,047,014 A | 9/1991 | Mosebach et al. | |
| 5,165,728 A * | 11/1992 | Mayer ........................ | 285/12 |
| 5,641,144 A | 6/1997 | Hendrickson et al. | |
| 6,059,245 A * | 5/2000 | Hermansen ............. | B62J 11/00 |
| | | | 248/311.2 |
| 6,220,557 B1 * | 4/2001 | Ziaylek et al. ............ | 248/316.1 |
| 6,277,277 B1 * | 8/2001 | Jacobi et al. ............... | 210/240 |
| 6,308,721 B1 | 10/2001 | Bock et al. | |
| 6,371,115 B1 | 4/2002 | Cewers et al. | |
| 6,630,068 B1 | 10/2003 | Vinci | |
| 6,883,766 B1 * | 4/2005 | Ziaylek et al. ............. | 248/313 |
| 7,138,053 B2 * | 11/2006 | Sato ............................ | 210/232 |
| 7,261,815 B2 * | 8/2007 | Cur et al. ................... | 210/232 |
| 7,294,262 B2 * | 11/2007 | Tadlock ..................... | 210/232 |
| 2008/0004788 A1 | 1/2008 | Dorfstatter et al. | |
| 2008/0047889 A1 * | 2/2008 | Huda .......................... | 210/234 |
| 2008/0302932 A1 | 12/2008 | Mosler et al. | |

FOREIGN PATENT DOCUMENTS

| | | |
|---|---|---|
| DE | 93201 51 U1 | 4/1995 |
| DE | 198 52 982 C1 | 3/2000 |
| DE | 19925297 C1 | 7/2000 |
| DE | 100 03 694 A1 | 8/2000 |
| DE | 69625352 T2 | 4/2003 |
| EP | 0665026 A2 | 8/1995 |
| EP | 1 057 493 A2 | 12/2000 |
| EP | 2 000 162 A1 | 12/2008 |
| JP | 2003505208 A | 2/2003 |
| JP | 2007029748 A | 2/2007 |
| JP | 2009-006109 A | 1/2009 |
| WO | 96/40315 A1 | 12/1996 |
| WO | 01/08722 | 2/2001 |

* cited by examiner

RETAINING MEANS FOR RETAINING AN EXTERNAL FUNCTIONAL MEANS ON A TREATMENT APPARATUS, EXTERNAL FUNCTIONAL MEANS, AND TREATMENT APPARATUS

CROSS REFERENCE TO RELATED APPLICATIONS

This application claims the benefit of U.S. Provisional Application No. 61/185,614 filed Jun. 10, 2009, and claims priority to German Patent Application No. 10 2009 024 448.4 filed Jun. 10, 2009 and German Patent Application No. 10 2009018 664.6 filed Apr. 23, 2009, all of which are herein incorporated by reference in their entirety.

FIELD OF INVENTION

The present invention relates to a retaining means for retaining at least one external functional means on a treatment apparatus. It further relates to an external functional means, as well as a treatment apparatus.

SUMMARY OF THE INVENTION

Apparatuses for treatment and analysis in medical or laboratory technology are regularly provided with external functional means. For their use, such external functional means are often retained or attached at the treatment or analytic apparatuses.

It is an object of the present invention to provide another retaining means for retaining an external functional means.

In the entirety of the following discussion, the use of the expression "may be or have" should preferably be understood to be synonymous with "preferably is or has."

The retaining means in accordance with the invention is suited for retaining at least one external functional means having at least two tube ports on a treatment apparatus.

To this end, the retaining means comprises at least two stops which restrict a rotational movement of the external functional means inside the retaining means.

The expression "rotational movement" as presently used is a rotational movement of the external functional means about an axis of rotation, in particular a longitudinal axis of the latter. Such rotational movement may be accompanied by further movements such as a translation. However, the movement to be restricted is, preferably predominantly characterized by a rotation.

An "axis of rotation" may here, in particular, be situated in a vertical plane (relative to the center of gravity of the Earth) and/or in particular be a direction of the main extension of the external functional means. The axis of rotation may correspond to the longitudinal axis of the external functional means.

The expression "stop" as presently used should be understood to be a component or an element of the retaining means which may bring about a limitation or restriction of a rotational movement. Such a stop may be a wall portion, a protrusion, a nose, or the like.

In a preferred embodiment of the retaining means in accordance with the invention, a twist of the external functional means is restricted to a maximum of between +5 and −5 degrees relative to a position of its use, a neutral position, an inserting position, or any other desired position of the external functional means inside the retaining means in accordance with the invention. Such a twist may preferably be restricted to a range of between +10 and −10 degrees. It may further be restricted to a range of between +20 and −20 degrees. Furthermore it may be restricted to ranges of between +30 and −30 degrees, between +40 and −40 degrees, between +50 and −50 degrees, between +60 and −60 degrees, between +70 and −70 degrees, between +80 and −80 degrees, between +90 and −90 degrees, as well as combinations and intermediate values of the given values and ranges.

In a further preferred embodiment of the retaining means of the invention, at least two tube ports of the external functional means are arranged at an angle relative to a vertical in the condition of use of the external functional means, or relative to a direction of the main extension thereof at the external functional means.

The expression "tube port" as presently used designates an arrangement or component provided for connecting, distributing and/or supplying that is suited for connecting the external functional means to a tube conduit. The tube port is in particular suited and intended for establishing a fluid connection.

Fluids which are considered in connection with the invention particularly include medical liquids such as blood and substituate, gases, emulsions, suspensions, solutions, in particular drug solutions, and the like.

The tube port may be a plug-in coupling such as, for example, a Hansen coupling, or a lug onto which such a coupling is attached in order to use the external functional means. However, in accordance with the invention, a tube lug or tube port may also be understood to be the combination of a lug (as part of the external functional means) and a connection means of the corresponding tube conduit connected thereto, for example a plug-in coupling.

The expression "plug-in coupling" should be understood to be an exemplary embodiment of a connection means for the connection to a "tube port." Whenever this is reasonable and applicable, connection means other than a plug-in coupling for establishing a fluid connection between the external functional means and a tube conduit may be employed.

The expression "tube conduit" as presently used designates a preferably flexible tube. The tube conduit may be coupled at its two ends to a tube fitting such as a flange, a threaded connection, and the like. In order to couple the tube conduit to a functional means, the tube fitting is connected to a tube port.

The tube conduit may, e.g., be a tube portion of an extracorporeal blood circuit such as, e.g., an arterial portion and/or a venous portion of an extracorporeal blood circuit. The tube conduit may be a conduit leading to a fluid container such as, e.g., a substituate container.

An "angle" of the arrangement of the tube ports may be any angle except zero or 180 degrees. In a preferred manner, the angle is situated in a range of (including) 45 to (including) 135 degrees. This means that the tube ports protrude in an arm-like manner from a base body of the external functional means, wherein, however, not all of the tube ports project from the base body in the direction of the main extension thereof.

Several or different tube ports may be arranged at an identical angle, however they may also be arranged at varying angles or angles that are different to each other.

In another preferred embodiment, the retaining means comprises a rotationally symmetrical base body. Then, by means of the stops provided on the retaining means in accordance with the invention, a rotation of the external functional means is restricted in the retaining means about the axis of rotation of the base body of the retaining means.

Limiting the admissible twist of the external functional means inside the retaining means may advantageously serve for protecting the tube conduits attached to the external functional means.

In another preferred embodiment, the retaining means comprises at least one lever or a lever means including at least one lever which pushes the external functional means inserted in the retaining means of the invention against a portion of the retaining means.

The expression "lever" as presently used designates a component or component part adapted to apply and/or transmit a retaining or holding force, respectively, to the external functional means. The lever may be disposed on a base body of the retaining means. The lever may be arranged perpendicular to a direction of the main extension of the retaining means or of the external functional means in the condition of use. It may exert a laterally acting holding force on the external functional means arranged in the retaining means of the invention.

The "holding force" may press the external functional means against the retaining means and prevent the external functional means from falling out of the retaining means.

In another preferred embodiment, the lever acts on the external functional means by means of a spring force.

The lever may be tensioned by a tensioning means, for example a spring, such that it tends to adopt a respective closed state at any time.

In another preferred embodiment, the retaining means comprises at least one cover means which restricts a shift of the external functional means along the direction of the main extension of the retaining means or along a vertical.

The expression "cover means" as presently used designates a means which provides a cover for the external functional means arranged in the retaining means of the invention. The cover means may, e.g., be a lid or a flap or the like. The cover means may be provided above and/or below the external functional means arranged in the retaining means of the invention. Preferably at least one cover means is provided above the external functional means.

The cover means may be connected to the base body and/or another portion of the retaining means. It can be connected to the retaining means in a movable way, e.g., in a liftable or rotatable manner. It can be connected to the retaining means in a rigid or non-deformable manner. It can be produced in one piece with a base body of the retaining means. It can be made of the same material as the base body.

The cover means provides a limitation or restriction of the movement or displaceability of the external functional means in a vertical direction.

In another preferred embodiment, the retaining means comprises a lining in at least one portion thereof.

A "lining" may comprise an elastic material or may consist thereof.

The expression "elastic material" as presently used designates a material having elastic properties, which may advantageously serve to provide a buffering effect when holding the external functional means in the retaining means of the invention. Suitable elastic materials include foamed materials, elastic resins, and the like. The elastic material may have anti-slip properties.

The elastic material may, for instance, be provided on the inner side of the base body facing the external functional means. The elastic material may, for instance, also or in addition be provided on the inner side of the cover means facing the external functional means. It may be provided on the lever means as a protection of the external functional means (e.g. when snapping the lever into place).

The lining or the elastic material may enhance holding or retaining the external functional means in the retaining means whereby the effect of the lever is amended.

In another preferred embodiment, the retaining means comprises at least one stop at or on which at least one tube port of the external functional means rests during its use.

The stop may, for example, be part of the base body or may be a portion of the latter and/or of the cover means or of a portion thereof.

In a preferred embodiment, the retaining means in accordance with the invention entirely or substantially consists of a base body, a lever means, and a connection means between the base body and the lever means which may optionally also be integrally formed with the base body and/or the lever means, or includes the above-mentioned components.

The expression "connection means" as presently used designates a means which is provided for connecting the base body to the lever means or to the lever of the retaining means.

This may be, for example, an articulation and/or a tensioning means which tensions the lever means or maintains a biased or tensioned state due to the material properties or by means of a spring means, such that the lever means may exert a spring effect on the external functional means arranged in the retaining means of the invention. By means of the spring effect, the external functional means may preferably be retained in the retaining means in accordance with the invention.

In another preferred embodiment, the retaining means in accordance with the invention comprises a mechanical coding for preventing incorrect insertion of an external functional means.

A "mechanical coding" may be a constructional provision such as, for example, arranging or mounting a means at the retaining means (e.g., at the cover means, at the base body, and/or at the lever of the retaining means). The configuration of this constructional provision may be such that it only admits the reception or mounting or arrangement of a matching part having a particular configuration, in accordance with a "key/lock principle." The configuration of this constructional provision may also be such that it only admits the insertion of the external functional means exclusively in a particular manner or in turn does not admit an insertion of certain other particular manners.

The retaining means in accordance with the invention may comprise a recess for inserting a connection means for the connection of a tube conduit to a tube port of the external functional means, of a handle of a plug-in coupling, in particular a Hansen coupling, or the like.

The recess provided with the retaining means in accordance with the invention may, for example, receive only a particular handle of a Hansen coupling. This may advantageously prevent incorrect insertion and/or coupling of an external functional means having two differently configured handles of the connection means to be used.

If the external functional means has several tube ports, for instance a Hansen coupling (in FIG. 1, e.g., at the lower tube port) of a tube port may be provided with a larger housing part and/or a cam. When the external functional means is correctly clamped in the retaining means, only a particular Hansen coupling (in FIG. 1, e.g., at the upper tube port) may be fitted into the recess without exerting any force. The larger housing part of the other Hansen coupling would, e.g., abut against the cover means and/or the lever and/or the lateral walls.

The tube ports of the external functional means may differ from each other in such a way that only particular connection means such as, e.g., Hansen couplings may be attached to a particular tube port. In case an external functional means is inserted in an inverse condition, this will at the latest be noted when connections using the connection means fail.

The recess and the handle of the Hansen coupling are preferably "marked" or "coded" such that they can only be held or arranged at the retaining means in the said combination, in particular if no force or brute force/violence is exerted.

In a further preferred embodiment, the retaining means is suited for holding or retaining an external functional means having at least two tube ports being present on different levels when using the external functional means. This may also advantageously prevent incorrect ("inverse") insertion of the external functional means.

The expression "level" as presently used refers to the arrangement or position of the tube ports of the external functional means on the latter and in particular to their respective positions along or in the direction of the main extension of the latter. The level may, however, in turn also refer to a vertical.

A level may, for example, designate the height of the respective tube port relative to a bottom side of the external functional means during its use.

The tube ports may also be arranged at a same level as regards the external functional means. They may be opposed to each other.

The position of the retaining means of the invention on a treatment apparatus may be selected such that short connecting tubes leading to other functional means of the treatment apparatus may be inserted or realized, respectively.

The retaining means in accordance with the invention may be employed for retaining or clamping an external medical or medical-technical functional means.

The object of the invention is equally achieved through an external, medical-technical functional means of the invention. All of the advantages achievable with the retaining means in accordance with the invention may also undiminishedly be achieved with the external functional means of the invention.

An "external functional means" may be a single-use component or a single-use article. It may be made of a plastic material.

The external functional means may be held and/or fastened on a treatment apparatus by means of a retaining means in accordance with the invention.

The external functional means may, for example, be connected to a blood conducting cassette. The external functional means may be connected to an extracorporeal blood circuit.

The connection between the external functional means and the extracorporeal blood circuit is preferably established by means of a plug-in coupling such as, for example, a Hansen coupling.

In a preferred embodiment, the external functional means or an extracorporeal blood circuit connected thereto therefore comprises a plug-in coupling, in particular a Hansen coupling.

The expression "plug-in coupling" as presently used designates a releasable tube coupling which is one example of a connection means. It may be configured as a so-called "Hansen coupling."

In another preferred embodiment, the external functional means comprises at least two variously or differently configured tube ports for connecting the external functional means to the tube conduits.

As was specified in the foregoing, this may, in particular, advantageously help to prevent interchanging the tube ports and thus incorrectly connecting the tube conduits to the external functional means.

The external functional means may comprise additional tube ports, in particular tube ports that do not come to lie in a portion or in an interior of the retaining means in accordance with the invention during its use. The external functional means may have four tube ports.

In another preferred embodiment, the plug-in coupling of the external functional means comprises at least one cam as is illustrated, for example, in FIG. 5 (where it is shown with two cams).

The external functional means of the invention may be intended for use in a treatment method. Treatment methods within the meaning of the present invention include medical or medical-technical treatment methods as well as analytic methods in laboratory technology.

Fluids, in particular liquids such as blood and/or substituate, may be conducted through the external functional means.

The external functional means may be a filter means. In a particularly preferred manner, the filter means is a blood treatment filter such as, for example, a dialysis filter.

The object of the invention is also achieved through a treatment apparatus of the invention. All the advantages of the retaining means of the invention may in turn undiminishedly be achieved with the treatment apparatus of the invention.

The treatment apparatus of the invention comprises at least one retaining means in accordance with the invention and/or an external functional means in accordance with the invention.

In a preferred embodiment of the present invention, the treatment apparatus is a blood treatment apparatus such as a dialyzing apparatus for performing a dialysis treatment, e.g., a hemodialysis, a hemofiltration, a hemodiafiltration, and the like.

The retaining means in accordance with the invention is suited for various sizes of external functional means, in particular for various diameters. It advantageously ensures that the external functional means may be ergonomically positioned and/or fixed in or on the treatment apparatus.

The retaining means in accordance with the invention advantageously ensures a defined insertion position of an external functional means having ports such as, for example, a dialyzer having lateral ports for blood and/or dialysate (e.g., model series FX of the company Fresenius Medical Care, Bad Homburg, Germany).

A possible twist of the external functional means may on the one hand advantageously be prevented via stops provided on the retaining means. On the other hand, the lateral walls of the base body or stops of the retaining means against which the tube ports of the external functional means abut advantageously serve to prevent or limit an excessive twist of the external functional means about its longitudinal axis.

In this way, a twist, a breakage, or even a tearing off of the tube conduits connected to the external functional means may advantageously be prevented. Furthermore, a so-called kinking of the tube conduits may also advantageously be avoided.

The risk of hemolysis due to breakage of the tubes or the tube conduits may thus advantageously be prevented securely.

The cover means of the retaining means may advantageously contribute to achieving a defined insertion of the external functional means in a vertical direction. This effect may advantageously be further enhanced by arranging the cover means with the upper edge of the spring-loaded lever via a form closure connection. In this way, any vertical slipping or shifting of the external functional means can be inhibited to a large extent, or can only be permitted in an admissible scope.

By arranging or providing an elastic material at the retaining means, it is advantageously possible to ensure a safe holding of the external functional means in the retaining means. In addition, the elastic material may minimize the risk of damage to the retaining means when snapping a lever into place.

The invention can also contribute to reducing noise during insertion and during operation of the external functional means. This may i.a. be effected by providing the elastic material.

Moreover, a mechanical coding, e.g., in form of recesses, for example in the cover means, ensures that coupling of the tube conduits, e.g., by means of plug-in couplings, may be realized in a defined and secure manner. In this way, confusing the tube conduits or hydraulic ports (supply/drain) may advantageously be avoided.

The cams may concurrently serve as stops in order to further limit a twist of the external functional means about its longitudinal axis.

The configuration of the retaining means in accordance with the invention is preferably chosen to be of a geometry without gaps and sharp edges. This may be achieved by manufacturing at least the base body of the retaining means as single-part component.

In this way, the retaining means in accordance with the invention may furthermore advantageously be cleaned in a simple and reliable manner. In addition, edges of the retaining means are preferably highly rounded, so that the risk of injuries of the operating personnel may advantageously be minimized.

The retaining means in accordance with the invention is preferably adapted to be sturdy, so that any careless disassembling of the external functional means will advantageously not result in any damage to the retaining means and/or the treatment apparatus.

The retaining means in accordance with the invention may advantageously also be operated with only one hand, e.g., the external functional means may be introduced into and removed from the retaining means again with only one hand.

Furthermore, the shape and/or position of the retaining means in accordance with the invention is advantageously selected such that the retaining means can not be damaged by a collision with an object, e.g. a door, in the assembled condition.

Due to its configuration, the filter retainer in accordance with the invention may advantageously be suited for several external functional means having different diameters like, e.g., dialysis filters.

As the tube ports may be supported on portions of the retaining means or rest thereon, by omitting a lower limitation of the external functional means within the retaining means of the invention, external functional means such as dialysis filters having different lengths may also be received.

BRIEF DESCRIPTION OF THE DRAWINGS

In the following, the present invention will be explained by means of example with reference to the appended drawings. In the drawings, identical reference numerals designate same or identical elements, wherein.

DETAILED DESCRIPTION OF THE DRAWINGS

Figure 1:
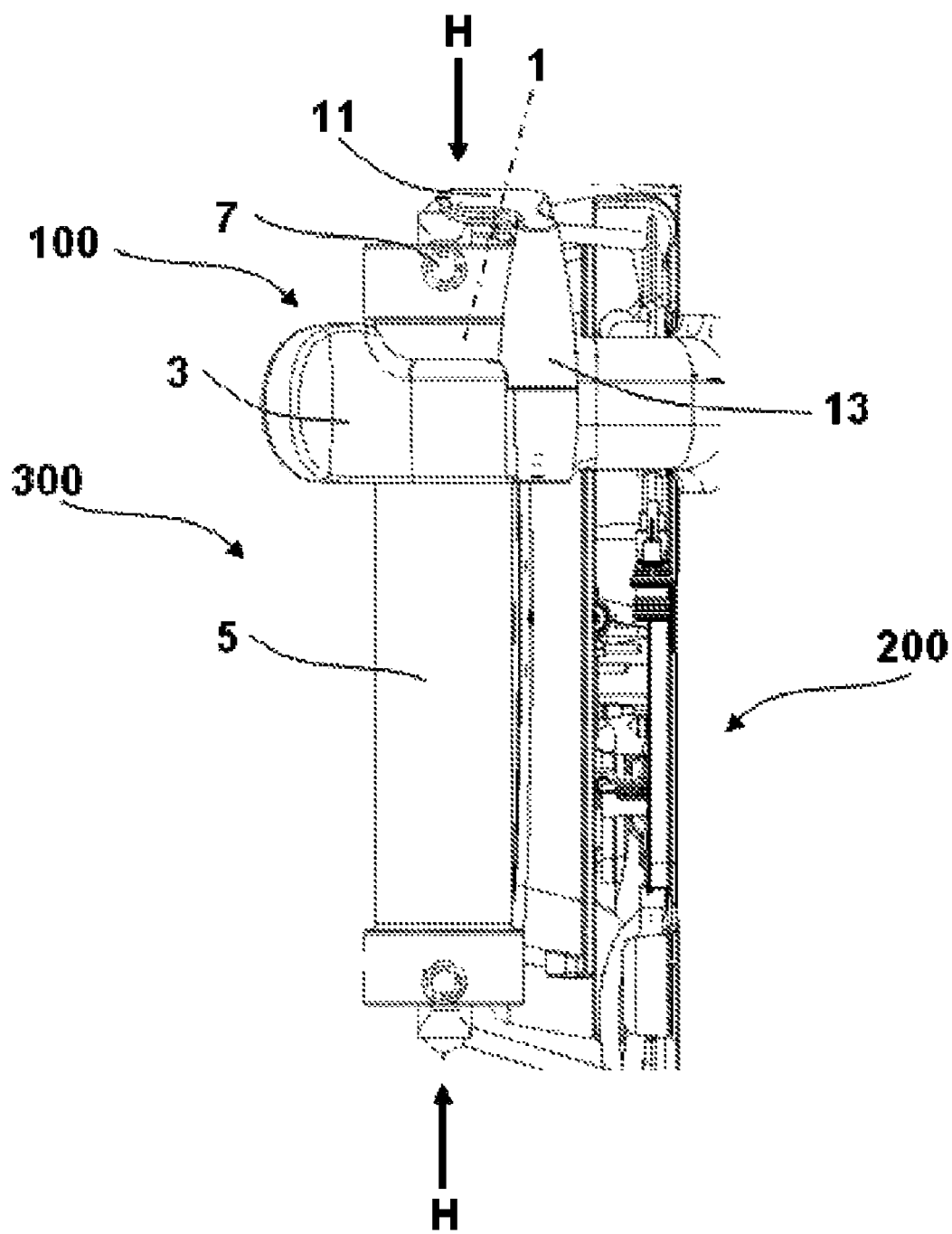
FIG. 1 shows a front view of a retaining means of the invention in accordance with a first embodiment.

FIG. 1 schematically shows a front view of a retaining means 100 of the invention in accordance with a first embodiment. The retaining means 100 comprises a base body 1. The retaining means 100 is part of a treatment apparatus 200. The retaining means 100 comprises a flap or a lever 3.

An external functional means 300, e.g., a dialysis filter, comprises a base body 5. The external functional means 300 comprises at least one first tube port 7 as well as a second tube port 9. The external functional means 300 is inserted in the retaining means 100 such as to abut against a cover means of the retaining means 100, e.g., a lid 11 at its upper side (as shown in the arrangement of FIG. 1). The lid 11 prevents shifting of the external functional means 300 along the direction of the main extension H of the retaining means 100 which is indicated by the arrows in FIG. 1.

The external functional means 300 is held in the retaining means 100 from the front side by means of the lever 3. The lever 3 is pushed against the base body 1 by a tensioning means, e.g., a spring 13. The external functional means 300 arranged in the retaining means 100 is therefore also pushed against the base body 1 from the front side and is thus retained in the retaining means 100.

Figure 2:
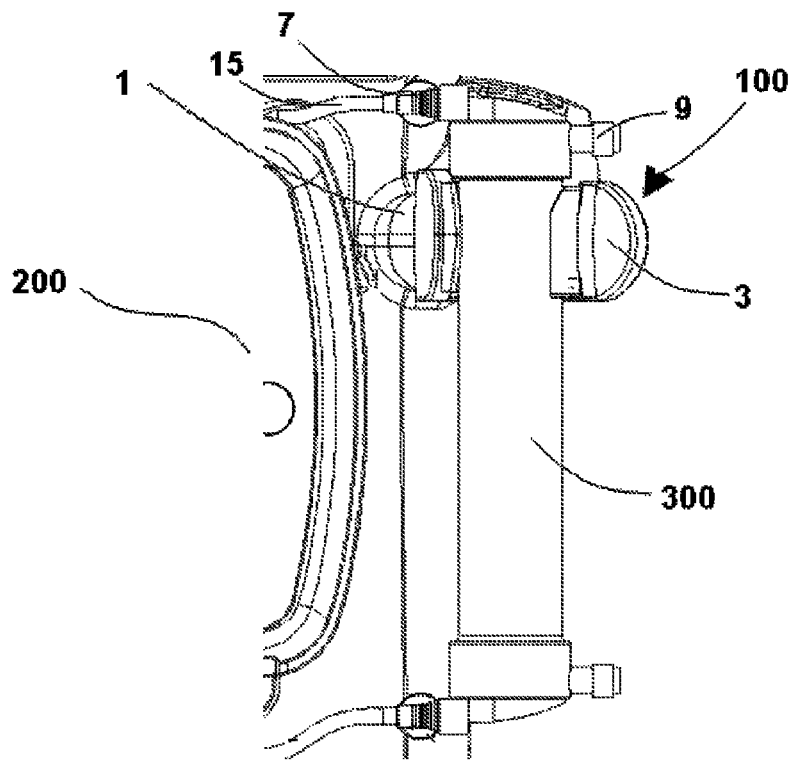
FIG. 2 shows a lateral view of the retaining means of the invention.

FIG. 2 shows a first lateral view of the retaining means 100 of the invention. As can be seen in FIG. 2, the lid 11 pushes the external functional means 300 or the base body 5 thereof against the base body 1 of the retaining means 100. In FIG. 2, the external functional means 300 is connected to a tube conduit 15.

The external functional means 300 further comprises two stops 23 and 24 against which the first tube port 7 and the second tube port 9 abut if the external functional means 300 arranged in the retaining means 100 is rotated further about its longitudinal axis than it is intended to. A tube conduit 15, e.g., a dialysate conduit, is connected to the external functional means 300. It is connected to the external functional means 300 by means of the first tube port 7.

Figure 3:
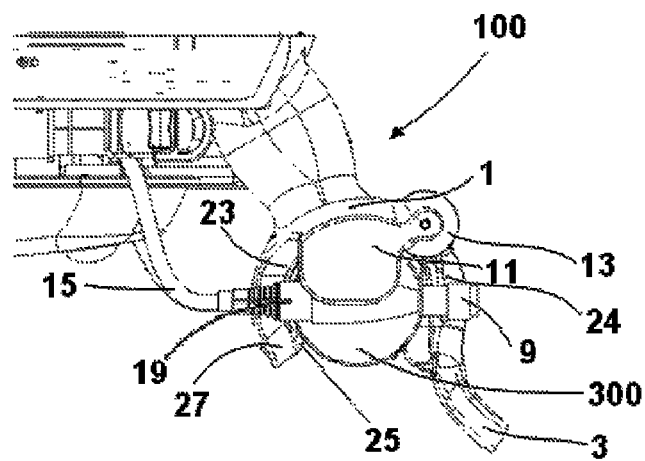
FIG. 3 shows a top view of the retaining means of the invention.

FIG. 3 shows a top view of the retaining means 100 of the invention. The retaining means 100 comprises a stop 23 against which a first Hansen coupling 19 abuts. The retaining means 100 comprises a lining, e.g., an elastic material 25, on a wall 27 of the base body 1. The elastic material 25 may on the one hand advantageously promote an anti-slip retention of the external functional means 300 in the retaining means 100; on the other hand it may serve as a cushioning for the protection of the external functional means 300.

As can be seen in FIG. 3, the external functional means 300 is retained on the treatment apparatus (not shown in FIG. 3) on substantially three sides via the base body 1 by the retaining means 100 in accordance with the invention. By simply pulling the external functional means 300, it is easily possible to remove the latter from the retaining means 100.

Figure 4:
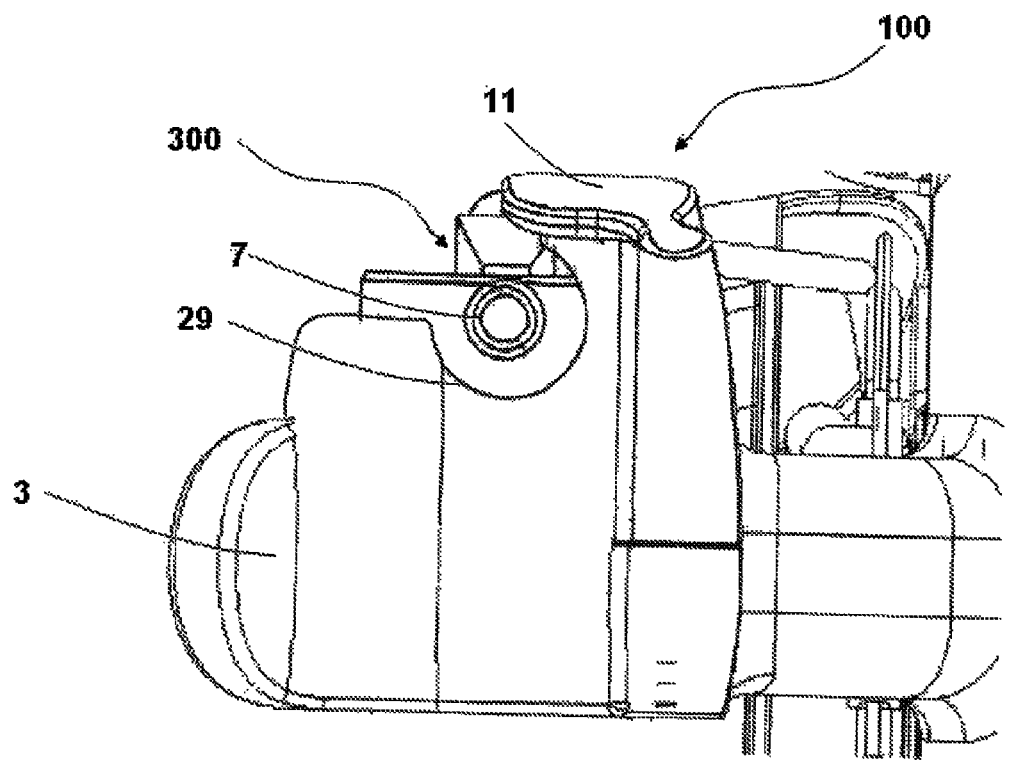
FIG. 4 shows an enlarged view of a portion of a retaining means of the invention in accordance with a second embodiment.

FIG. 4 shows a detail or portion of a retaining means 100 of the invention in accordance with a second embodiment. The retaining means 100 has a recess 29. The recess 29, presently shown as a ¾-circle recess, represents a part of a cross-coupling safeguard. It is arranged about the first tube port 7. The recess 29 acts as a mechanical coding and makes sure that the external functional means 300 is correctly connected for the condition of its use. If, for example, a connection of the external functional means 300 by means of plug-in couplings is provided, the recess 29 may be configured such that it may receive only a quite particular type and/or configuration of a plug-in coupling to thus admit coupling of the external functional means 300.

Figure 5:
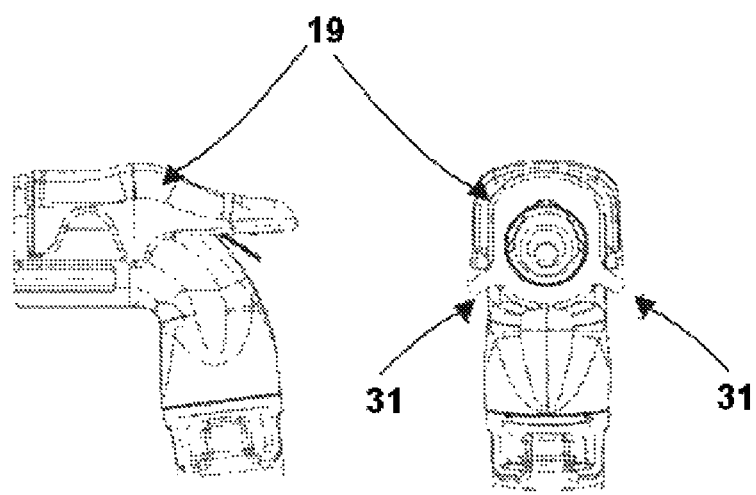
FIG. 5 shows a Hansen coupling.

FIG. 5 shows an example of such a plug-in coupling having the shape of a Hansen coupling. FIG. 5 exemplarily shows the configuration of the first Hansen coupling 19. The Hansen coupling 19 comprises two protrusions or cams 31 on its upper side (see top view of the right-hand representation in FIG. 5). The cams 31 are provided for admitting the first Hansen coupling 19 only to be arranged in a particular position of the retaining means, e.g. in accordance with the representation in FIG. 2, on top at the external functional means 300. In this way, an incorrect connection or coupling of tube conduits to the external functional means may advantageously be avoided. At the same time, the cams 31 can serve as stops to prevent any arbitrary twist of the external functional means 300 about its longitudinal axis.

In certain embodiments, the retaining means according to the invention is advantageously suited to receive differently designed external functional means, e.g., dialyzers—without having to be modified itself in its construction. However, in other embodiments, the retaining means according to the invention can also be adapted to the type and/or the configuration/the construction of the external functional means intended to be received or retained, respectively.

Figure 6:
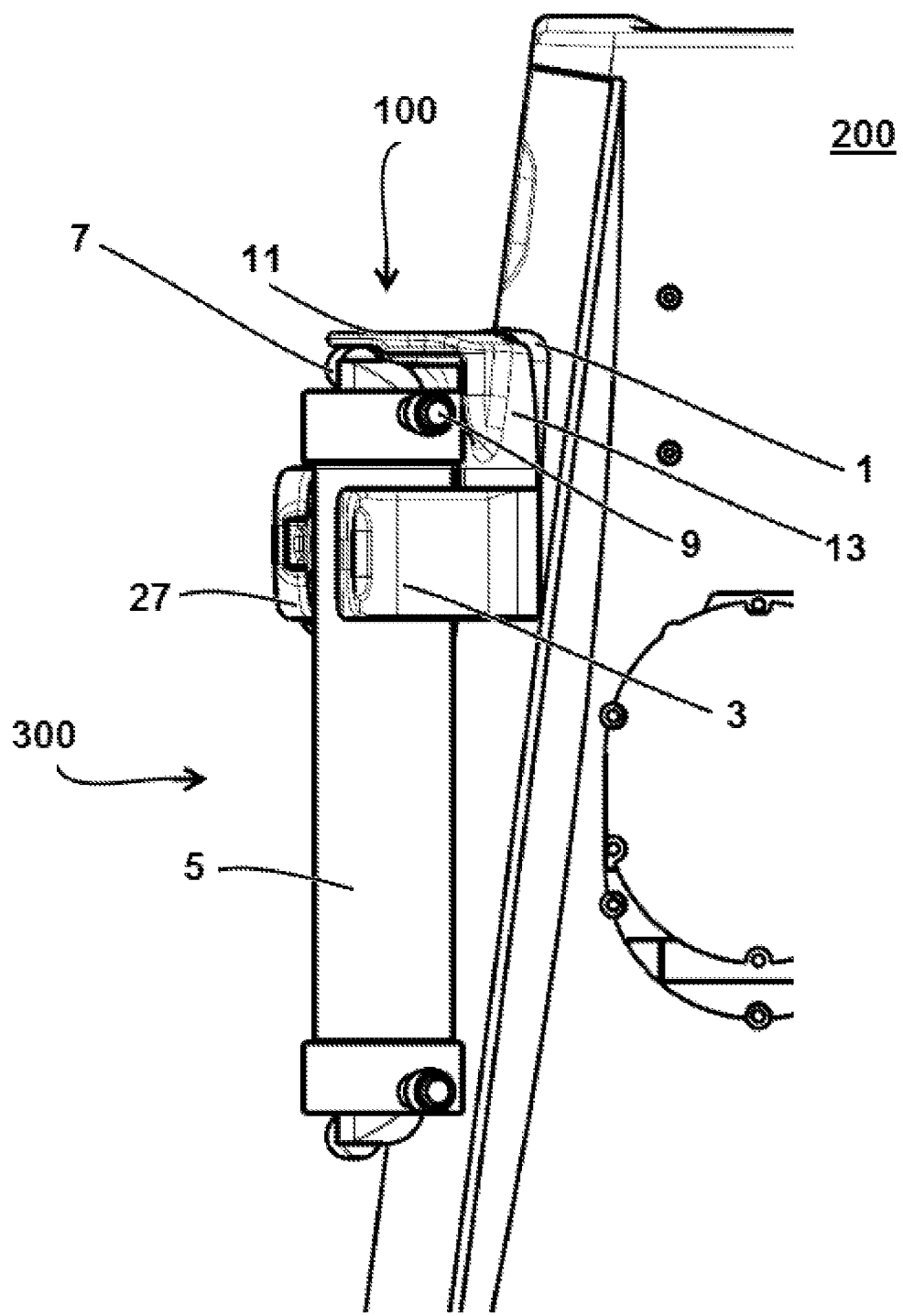
FIG. 6 shows a front view of the retaining means according to the invention with an external functional means in the form of a dialysis filter for adults.
Figure 7:
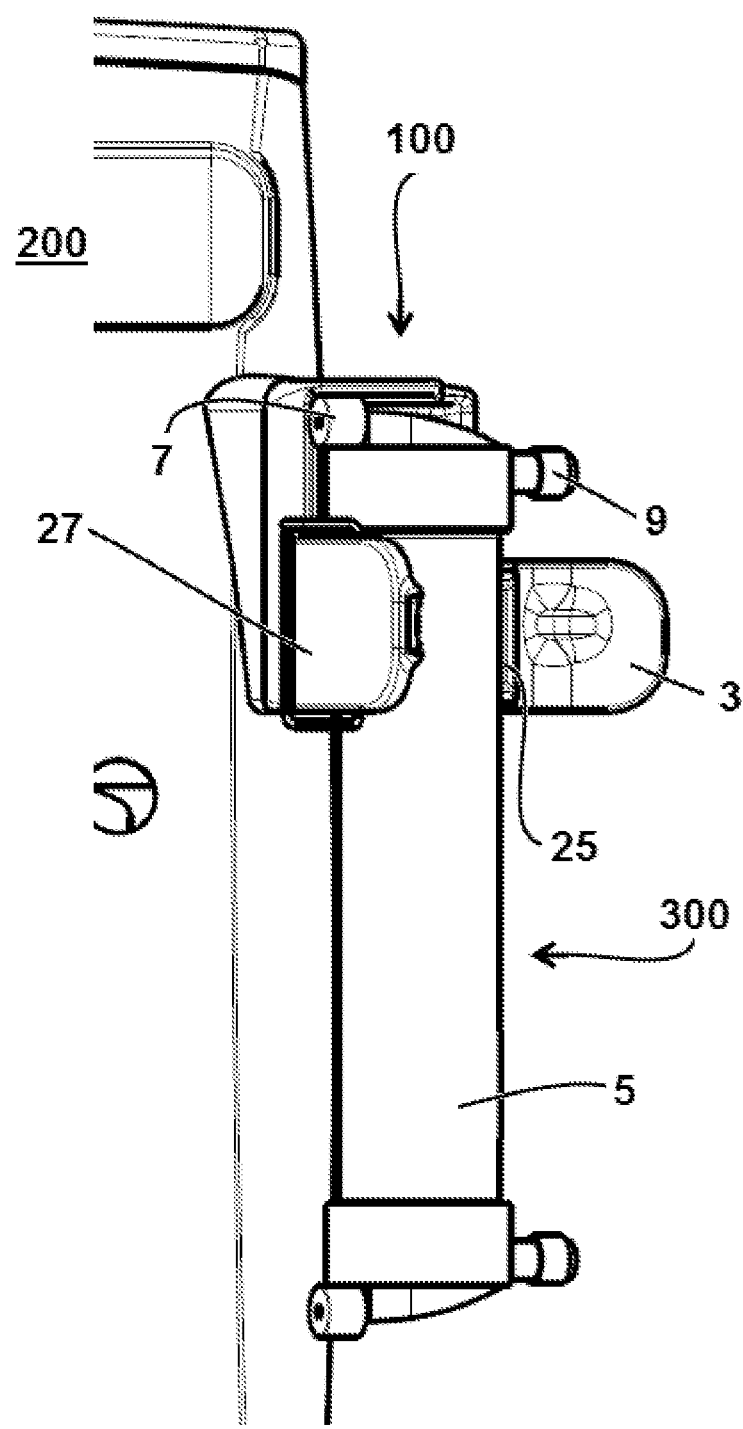
FIG. 7 shows a side view of the retaining means according to the invention with the external functional means of FIG. 6.
Figure 8:
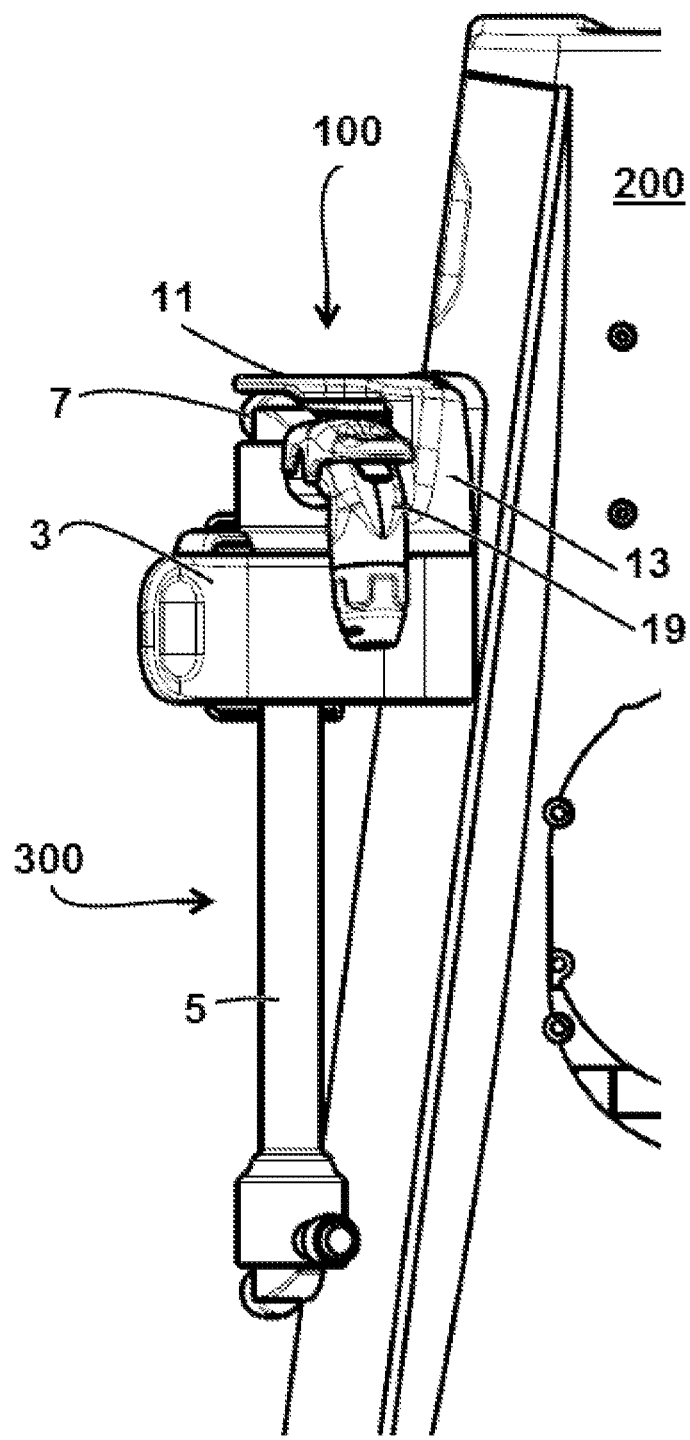
FIG. 8 shows a front view of the retaining means according to the invention with an external functional means in the form of a dialysis filter for children.
Figure 9:
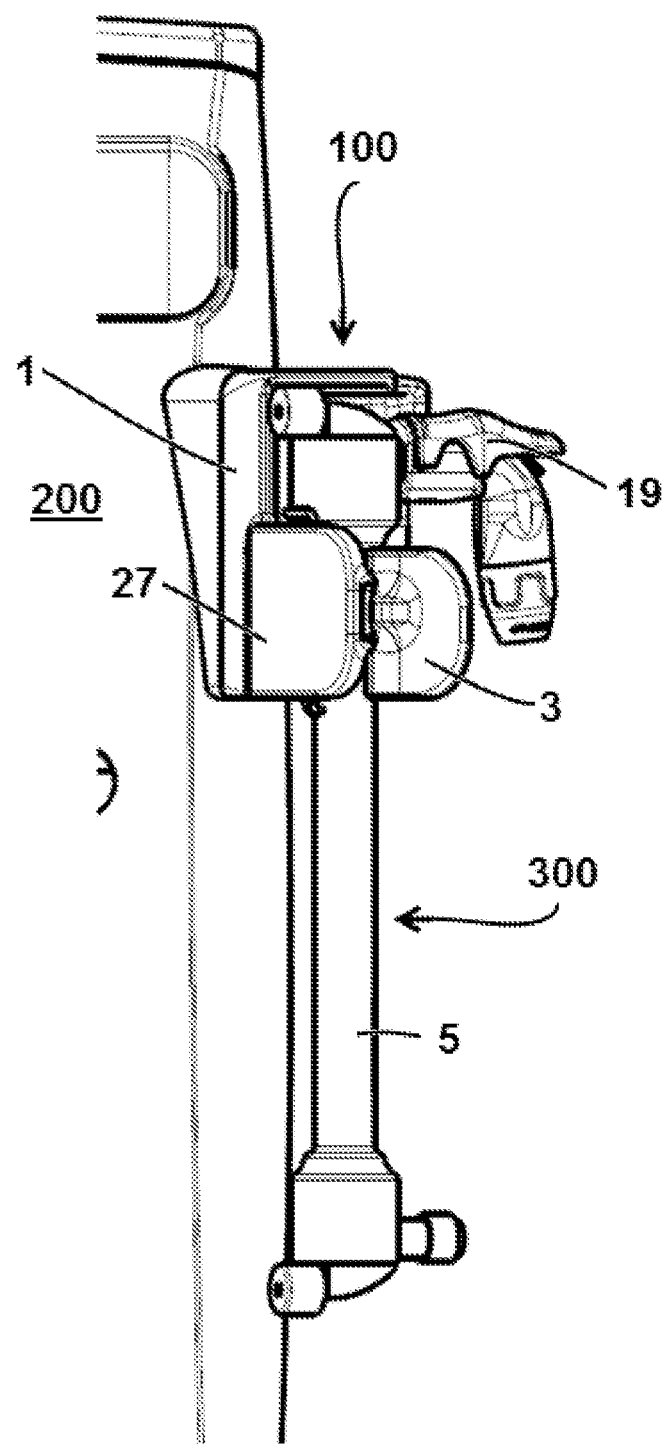
FIG. 9 shows a side view of the retaining means according to the invention with the external functional means of FIG. 8.

FIGS. 6 and 7 and FIGS. 8 and 9 in which the retaining means 100 is shown in a front section top right of the treatment apparatus 200 in a view on the front side of the treatment apparatus 200 demonstrate how one and the same retaining means according to the invention which is substantially identical in both the FIGS. 6, 7 and the FIGS. 8, 9 (the retaining means may optionally include differently designed details that are, however, insignificant for the relevant aspects of fixation) is able to receive two differently designed external functional means—each at a different point of time. As individual components as well as the way of how the external functional means is fixed to the retaining means according to the invention substantially or completely correspond to the embodiments described with respect to the foregoing figures, it is referred to the above-mentioned embodiments in order to avoid repetitions.

FIG. 6 shows a front view of the retaining means according to the invention with an external functional means 300 in the form of a dialysis filter for adults, e.g., a dialyzer of the FX 120 type of the company Fresenius Medical Care Deutschland GmbH, Germany. FIG. 7 shows a side view of the retaining means according to the invention with the external functional means of FIG. 6.

FIG. 8 shows a front view of the retaining means according to the invention with an external functional means in the form of a dialysis filter for children, e.g., a pediatric dialyzer of the FX type of the company Fresenius. FIG. 9 shows one respective side view. As shown in FIGS. 8 and 9, the external functional means 300 comprises a Hansen coupling 19 at a second tube connection (hidden in FIGS. 8 and 9).

As compared to the external functional means 300 of FIGS. 6 and 7, the external functional means 300 in FIGS. 8 and 9 is clearly slighter. Due to the retaining means according to the invention which is advantageously suited for receiving differently designed external functional means, it is possible to retain both the thicker dialysis filter for adults and the thinner dialysis filter for children in a force closure or frictional connection and slipping-safe manner.

Figure 10:
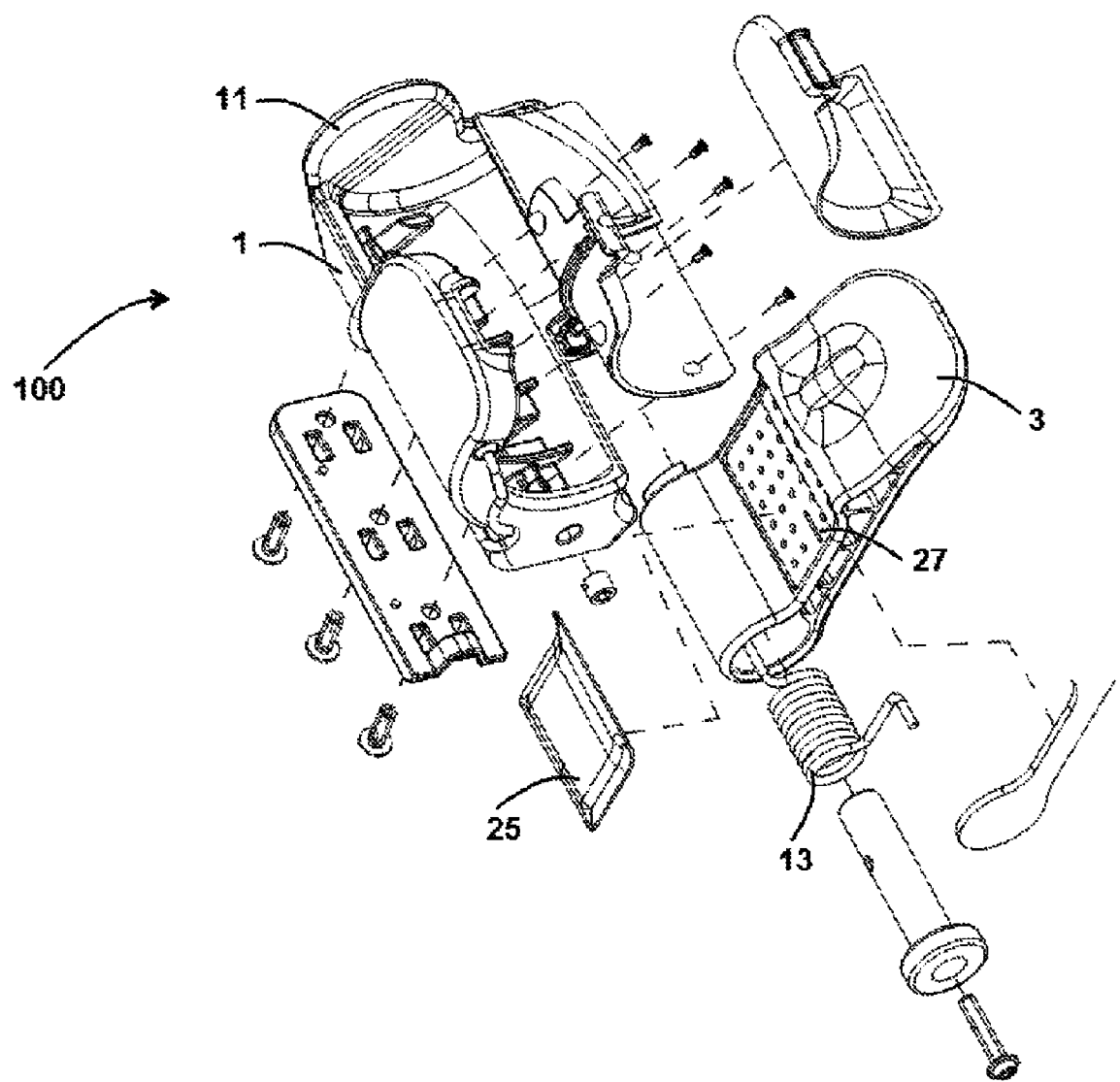
FIG. 10 shows an exploded view of a retaining means according to the invention.
Figure 11:
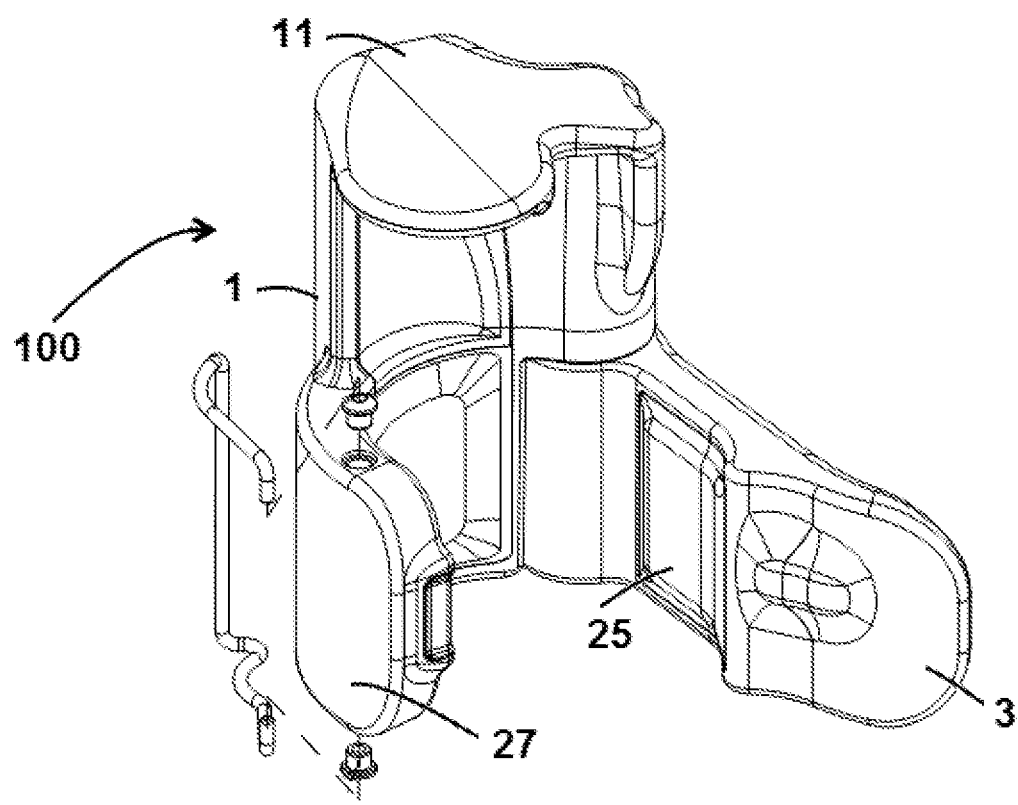
FIG. 11 shows a perspective view (from the front and top) of a retaining means according to the invention.
Figure 12:
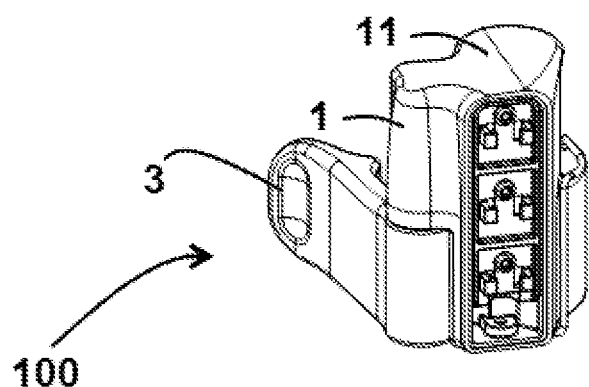
FIG. 12 shows a perspective view (from behind and top) of a retaining means according to the invention.

FIG. 10 shows an exploded view of a retaining means according to the invention which exemplifies a way of assembling the retaining means. A retaining means assembled according to the exemplary embodiment of FIG. 10 is shown in a perspective view from the front and top in FIG. 11 and in a perspective view from behind and top in FIG. 12.

We claim:

1. A system for retaining at least one blood treatment filter on a blood treatment apparatus comprising:
   the at least one blood treatment filter comprising at least two tube ports configured for coupling to tube conduits; and
   a retaining device comprising at least two stops that restrict a rotational movement of the at least one blood treatment filter inside the retaining device;
   wherein the retaining device further comprises:
      one cover device for preventing or restricting a shift of the blood treatment filter along a direction of main extension of the retaining device or along a vertical direction,
      wherein at least one tube port of the blood treatment filter rests on at least one stop of the retaining device during use,
      at least one lever,
      a base body, and
      a connection device connecting the at least one lever and the base body directly wherein the connection device is or comprises a spring,
      wherein said lever is configured to push the blood treatment filter against the base body via a lateral acting force of the spring; and
      wherein the blood treatment filter is retained on the blood treatment apparatus on only substantially three lateral sides, out of four total lateral sides of the blood treatment filter, by the retaining device.

2. The system according to claim 1, wherein the at least two tube ports of the blood treatment filter are arranged on the blood treatment filter at an angle with a vertical or at an angle with the direction of main extension during use.

3. The system according to claim 1, wherein the base body is a rotationally symmetrical base body,
wherein a twist of the blood treatment filter in the retaining device about the axis of rotation of the base body thereof is restricted by the at least two stops.

4. The system according to claim 3, wherein the restricted twist of the blood treatment filter is for protecting the tube conduits adapted to be coupled to the blood treatment filter.

5. The system according to claim 1, wherein the lever acts on the blood treatment filter via the spring.

6. The system according to claim 1, wherein the retaining device further comprises:
a wall having a lining in at least one portion thereof.

7. The system according to claim 1, wherein the retaining device further comprises:
a mechanical coding for preventing incorrect insertion of the blood treatment filter.

8. The system according to claim 1, wherein the retaining device further comprises:
a recess for the insertion of a handle of a plug-in coupling.

9. The system according to claim 1, wherein the blood treatment filter further comprises:
at least one plug-in coupling.

10. The system according claim 1, wherein the at least two tube ports of the blood treatment filter are arranged on different levels.

11. The system according to claim 1, wherein the blood treatment filter is connected to an extracorporeal blood circuit.

12. The system according to claim 1, wherein the at least two tube ports include at least two different types of tube ports for connecting the blood treatment filter to the tube conduits.

13. The system according to claim 9, wherein the at least one plug-in coupling comprises at least one cam.

14. A blood treatment apparatus comprising: the system of claim 1.

15. The system according to claim 1, wherein the blood treatment apparatus is a dialysis apparatus.

16. The system according to claim 1, wherein the base body and the at least one lever are separate components that are connected to one another.

17. The system according to claim 1, wherein the spring is directly connected to the base body.

* * * * *

UNITED STATES PATENT AND TRADEMARK OFFICE
CERTIFICATE OF CORRECTION

| | |
|---|---|
| PATENT NO. | : 9,579,438 B2 |
| APPLICATION NO. | : 12/765940 |
| DATED | : February 28, 2017 |
| INVENTOR(S) | : Jurgen Haecker and Uwe Lapp |

It is certified that error appears in the above-identified patent and that said Letters Patent is hereby corrected as shown below:

In the Claims

Column 12, Line 4, Claim 10, after "according" insert --to--.

Signed and Sealed this
Second Day of May, 2017

Michelle K. Lee
*Director of the United States Patent and Trademark Office*